(12) United States Patent
Ranta et al.

(10) Patent No.: US 9,199,050 B2
(45) Date of Patent: Dec. 1, 2015

(54) ARRANGEMENT AND METHOD FOR GUIDING EXPIRED RESPIRATORY GAS FLOW USING GAS ROUTING DEVICE

(75) Inventors: Janne Ranta, Espoo (FI); Niklas Arkima, Espoo (FI)

(73) Assignee: CAREFUSION CORPORATION, San Diego, CA (US)

( * ) Notice: Subject to any disclaimer, the term of this patent is extended or adjusted under 35 U.S.C. 154(b) by 712 days.

(21) Appl. No.: 13/459,339

(22) Filed: Apr. 30, 2012

(65) Prior Publication Data

US 2013/0284175 A1  Oct. 31, 2013

(51) Int. Cl.
  *A62B 7/10* (2006.01)
  *A62B 19/00* (2006.01)
  *A62B 23/02* (2006.01)
  *A61M 16/01* (2006.01)
  *A61M 16/22* (2006.01)
  *A61M 16/08* (2006.01)
  *A61M 16/20* (2006.01)

(52) U.S. Cl.
  CPC ........... *A61M 16/01* (2013.01); *A61M 16/0891* (2014.02); *A61M 16/22* (2013.01); *A61M 16/208* (2013.01); *A61M 2205/587* (2013.01); *A61M 2205/60* (2013.01); *A61M 2205/7581* (2013.01)

(58) Field of Classification Search
  None
  See application file for complete search history.

(56) References Cited

U.S. PATENT DOCUMENTS

| | | | | |
|---|---|---|---|---|
| 3,923,057 A | * | 12/1975 | Chalon | 128/203.16 |
| 5,694,924 A | * | 12/1997 | Cewers | 128/204.21 |
| 6,213,120 B1 | * | 4/2001 | Block et al. | 128/204.23 |
| 6,536,433 B1 | * | 3/2003 | Cewers | 128/205.24 |
| 7,762,255 B2 | | 7/2010 | Mills | |
| 2007/0144516 A1 | * | 6/2007 | Doyle | 128/204.18 |
| 2007/0163591 A1 | * | 7/2007 | Ross et al. | 128/205.12 |

FOREIGN PATENT DOCUMENTS

| | | |
|---|---|---|
| EP | 1048313 A2 | 11/2000 |
| EP | 1 230 943 A2 | 8/2002 |
| WO | 03/063751 A2 | 8/2003 |

OTHER PUBLICATIONS

Search Report from GB Application No. 1307625.2 dated Oct. 18, 2013.
United Kingdom Examination Report for United Kingdom Application No. GB1307625.2, dated Apr. 14, 2015, 1 page.

* cited by examiner

*Primary Examiner* — Jackie T Ho
*Assistant Examiner* — Eric Bryant
(74) *Attorney, Agent, or Firm* — McDermott Will & Emery LLP

(57) ABSTRACT

An arrangement and method for guiding expired gas flow in a breathing circuit through a housing assembly for removing an undesired gas component is disclosed herein, The housing assembly includes a first port and a second port, one of the ports receiving the flow and another discharging the flow. The arrangement includes a gas routing device in flow communication with the breathing circuit and the housing assembly. The routing device is provided with at least two different route options. According to a first option the gas is guided to the first port and through the housing assembly to the second port and to the gas routing device for guiding for the inspiration. According to a second option the gas is guided to the second port and through the housing assembly to the first port and to the gas routing device for guiding for the inspiration.

18 Claims, 3 Drawing Sheets

ARRANGEMENT AND METHOD FOR GUIDING EXPIRED RESPIRATORY GAS FLOW USING GAS ROUTING DEVICE

BACKGROUND OF THE INVENTION

The disclosure relates generally to an arrangement and method for guiding expired respiratory gas flow in a breathing circuit through a housing assembly for removing an undesired expired gas component of the respiratory gas flow before conveying for an inspiration of a subject. The housing assembly comprises a first port and a second port, one of the ports being for receiving the gas flow and another of the ports being for discharging the gas flow. The disclosure also relates to a breathing circuit for ventilating lungs of a subject.

Anesthesia machines are optimized for delivering anesthesia to a patient using volatile anesthetic agent liquids. In such systems, the anesthetic agent is vaporized and mixed into the breathing gas stream in a controlled manner to provide a gas mixture for anesthetizing the patient for a surgical operation. The most common volatile anesthetic agents are halogenated hydrocarbon chains, such as halothane, enflurane, isoflurane, sevoflurane and desflurane. Additionally, nitrous oxide ($N_2O$) can be counted in this group of volatile anesthetic agents, although the high vapor pressure of nitrous oxide causes nitrous oxide to vaporize spontaneously in the high pressure gas cylinder, wherefrom it can be directly mixed as gas with oxygen. The anesthetizing potency of nitrous oxide alone is seldom enough to anesthetize a patient and therefore another volatile agent is used to support that.

Since the volatile anesthetic agents are expensive, they are effective greenhouse gases and further harmful to the atmospheric ozone layer, anesthesia machines have been developed to minimize the consumption of the gases. To keep patients anesthetized, a defined brain partial pressure for the anesthetic agent is required. This partial pressure is maintained by keeping the anesthetic agent partial pressure in the lungs adequate. During a steady state, the lung and body partial pressures are equal, and no net exchange of the anesthetic agent occurs between the blood and the lungs. However, to provide oxygen and eliminate carbon dioxide, continuous lung ventilation is required.

Anesthesia machines are designed to provide oxygen to the patient and eliminate carbon dioxide ($CO_2$), while preserving the anesthetic gases. To meet these goals a re-breathing circuit is used. In this patient exhaled gas is reintroduced for inhalation. Before re-inhalation carbon dioxide must be removed from the gas, which is done with a carbon dioxide absorber. Before inhalation, the gas is supplied with additional oxygen and anesthetic agents based upon the patient demand. In this arrangement, the additional gas flow added to the re-breathing circuit can be less than 0.5 L/min although the patient ventilation may be 5-10 L/min. Such ventilation of the lung is carried out using a ventilator pushing inhalation gas with overpressure to patient lungs and then allowing that to flow out passively from the pressurized lungs to the breathing circuit.

Ventilation carries the breathing circuit oxygen to lungs for uptake to be burned in body metabolism. The outcome of this is $CO_2$ that blood circulation transports to lungs wherefrom it becomes carried out with exhalation gas. Before re-inhalation the gas is guided through absorber for $CO_2$ removal. Effective $CO_2$ removal requires close contact with the breathing gas and the removing substance. To provide large contact area, the removing substance is therefore a surface of porous structure of granules that fill the cartridge. The form of this granular structure is guided by the flow resistance, the limitation of which is one key design goals of the breathing circuit. In absorber optimized for minimal resistance the gas flow path through the stacked granules is short and the flow distributes to wide area. In such structure the gas flows slowly because of large surface area providing time for reaction between the gas and absorbent granules.

Absorber canisters have two gas connections: One inlet for the gas flow carrying carbon-dioxide and one outlet. Between inlet and outlet the canister has a gas pathway. The absorber granules form part of this pathway during which the carbon dioxide is removed from the gas.

The $CO_2$ absorption is based on chemical reaction in the absorption cartridge. Typically the reaction is based on the use of alkaline chemicals often referred as soda lime (mainly including calcium hydroxide) that react with aqueous $CO_2$. Typical end results of this exothermic reaction are calcium carbonate and water. The air exhaled by the patient includes approximately 5% of $CO_2$. A fresh absorber is able to purify the breathing air from $CO_2$ virtually completely. When the absorption capacity is getting exhausted there is a gradual increase of $CO_2$ in the air downstream the absorber. A typical clinical practice is that latest when the inspiratory air reaches $CO_2$ content of 0.5% the absorber unit needs to be replaced.

The $CO_2$ absorption takes place in the soda lime bed inside the absorber cartridge. Depending on the absorber, such as container geometry, absorbent chemistry and grain characteristics, and the clinical factors, such as the amount of exhaled $CO_2$, respiratory rate, etc, as well as the anesthesia machine set ups, such as used fresh gas flow, the absorbent volume and specifically the absorbent bed height required for complete $CO_2$ removal change. This height or zone in the absorbent bed required for appropriate absorption of $CO_2$ is often referred as "mass transfer zone". Due to the characteristics of the absorption reaction and specifically the mass transfer zone a single absorber unit always includes a remarkable amount of unused absorbent at the time when it needs to be replaced to maintain below 0.5% $CO_2$ levels since the required mass transfer zone at that moment is bigger than there is fresh absorbent remaining.

The problems related to the inability to fully use a single absorber do not exist in all anesthesia machine designs, in case there are two identical absorber units on top of each other. The absorbers are not intended to be replaced simultaneously but individually only after the individual absorber is fully exhausted. In practice this is accomplished by having the more exhausted absorber being exposed to the $CO_2$ rich gas first. Even when it reaches the point where it has not enough capacity to absorb all the $CO_2$ the second more fresh unit downstream is still capable of absorbing the remaining $CO_2$. When the first absorber is fully exhausted it should be removed and the other partially used absorber can be mounted to the place where the first absorber used to be and a new fresh absorber is placed to the spot where the second absorber used to be. And the absorber changing cycle starts over again. On the other hand there are some concerns that the benefits of a twin absorber design may not be fully exploited if it is not easy or intuitive enough how to manage the swapping of the absorber units. Specifically, how to make secure the right absorber unit is moved from one port to another and that the right unit replaced with a new one.

However, there are some benefits with the more recently developed single absorber designs over the twin absorber assembly. One of them is the fact that in the single absorber designs available in the market place the gas return path is integrated into the absorber assembly and hence they require no additional conduit for return gas. In the well-known twin absorber design the gas return conduit is a part of the anesthesia machine—not integrated into the absorber. This means that even if a care giver uses disposable twin absorbers that are not serviced but simply disposed after use there still is the gas return conduit in the anesthesia machine that needs cleaning to avoid cross contamination. Also, all the parts in the breathing circuit add up the total air volume. However, a minimized air volume is preferable. The benefits include smaller total amount of anesthetic agents required as well as smaller system gas compliance.

BRIEF DESCRIPTION OF THE INVENTION

The above-mentioned shortcomings, disadvantages and problems are addressed herein which will be understood by reading and understanding the following specification.

In an embodiment, an arrangement for guiding expired respiratory gas flow in a breathing circuit through a housing assembly for removing an undesired expired gas component of the respiratory gas flow before guiding for an inspiration of a subject, the housing assembly having a first port and a second port, one of the ports being for receiving the gas flow and another of the ports being for discharging the gas flow, includes a gas routing device in flow communication with the breathing circuit and the housing assembly through the first port and the second port. The routing device is provided with at least two different route options, a first route option is configured to guide the expired gas first to the first port of the housing assembly and through the housing assembly to the second port of the housing assembly and to the gas routing device for guiding along the breathing circuit for the inspiration, a second route option is configured to guide the expired gas first to the second port of the housing assembly and through the housing assembly to the first port of the housing assembly and to the gas routing device for guiding along the breathing circuit for the inspiration.

In another embodiment, a breathing circuit for ventilating lungs of a subject includes a first limb for guiding expired respiratory gas, and a housing assembly having a first port and a second port, one of the ports being for receiving the expired gas flow and another of the ports being for discharging the gas flow, the ports allowing the expired respiratory gas flow through the housing assembly to remove an undesired expired gas component of the respiratory gas flow. The breathing circuit for ventilating lungs of a subject also includes a second limb for guiding the respiratory gas received from the housing assembly for an inspiration, and an arrangement for guiding expired respiratory gas flow through the housing assembly before conveying for an inspiration. The arrangement comprising a gas routing device in flow communication with the first limb, the second limb and the housing assembly through the first port and the second port, the routing device being provided with at least two different route options, a first route option being configured to guide the expired gas first to the first port of the housing assembly and through the housing assembly to the second port of the housing assembly and to the gas routing device for guiding along the second limb for the inspiration, a second route option being configured to guide the expired gas first to the second port of the housing assembly and through the housing assembly to the first port of the housing assembly and to the gas routing device for guiding along the second limb for the inspiration.

In yet another embodiment, a method for guiding expired respiratory gas flow in a breathing circuit through a housing assembly for removing an undesired expired gas component of the respiratory gas flow before guiding for an inspiration of a subject, the housing assembly having a first port and a second port, one of the ports being for receiving the gas flow and another of the ports being for discharging the gas flow, includes choosing from at least two different route options the expired respiratory gas flow through the housing assembly. A first route option is configured to guide the expired gas first to the first port of the housing assembly and through the housing assembly to the second port for guiding along the breathing circuit for the inspiration. A second route option is configured to guide the expired gas first to the second port of the housing assembly and through the housing assembly to the first port of the housing assembly for guiding along the breathing circuit for the inspiration.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
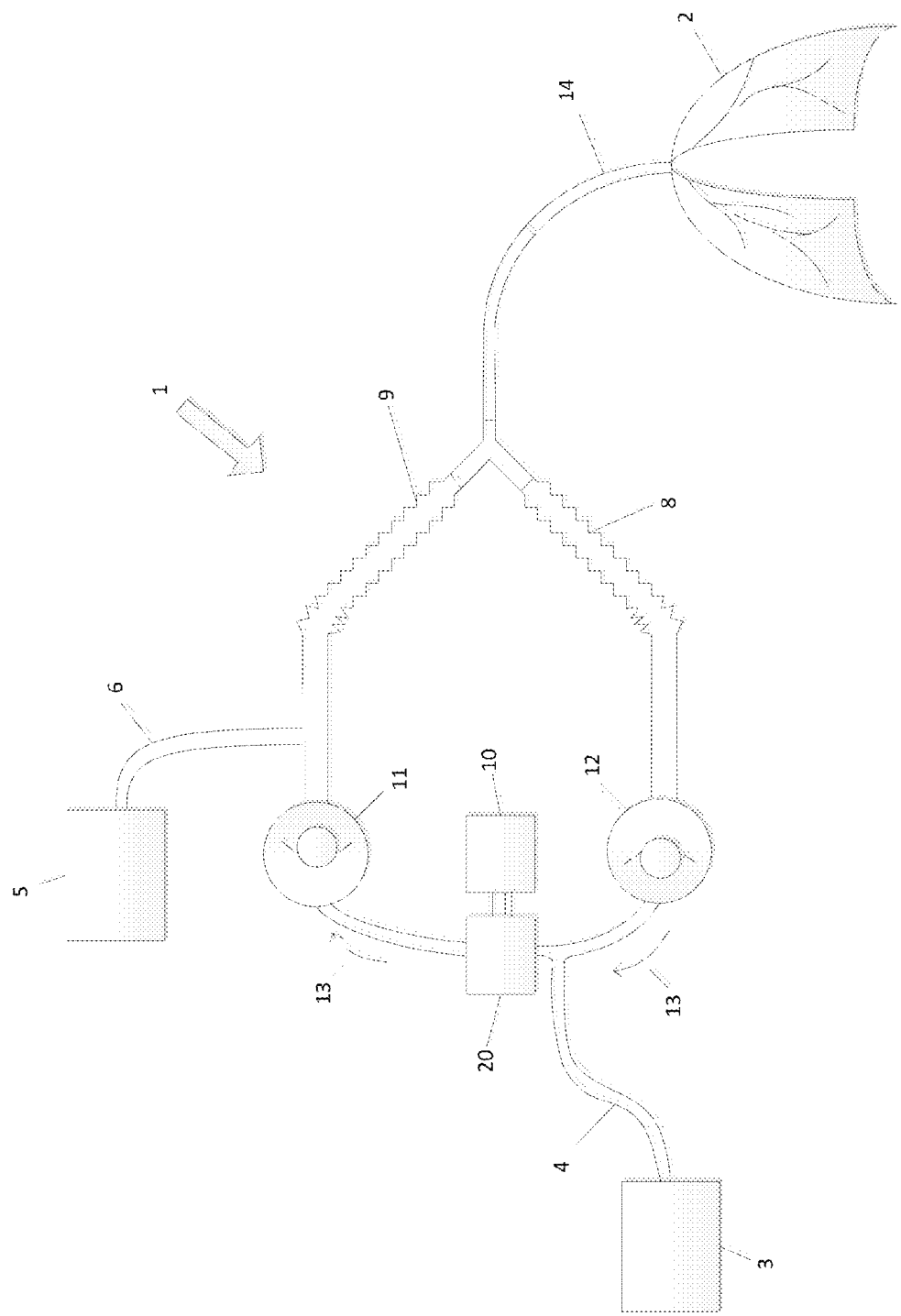
FIG. 1 shows a schematic view of a breathing circuit for ventilating lungs of a subject.

In FIG. 1 a breathing circuit 1 for ventilating lungs 2 of a subject is disclosed. The breathing circuit comprises a ventilator 3 supplying along a ventilator connection 4, such as a ventilator tube, breathing gas to the lungs for an inspiration and receiving breathing gas for expiration. The ventilator may be whichever well-known type e.g. drive gas based pneumatic flow-valve or mechanical piston driven. Also the breathing circuit comprises a gas mixer 5 supplying a fresh gas in this specific embodiment along a fresh gas tube 6 for the subject breathing. The gas mixer may comprise an anesthetic agent supply (not shown in the Figure) such as an anesthetic agent vaporizer providing anesthetic agent for the subject breathing.

The breathing circuit 1, which may be a re-breathing circuit, comprises also a first limb 8, such as an expiration limb, discharging an expiration gas and a second limb 9, such as an inspiration limb, providing an inspiration gas including the fresh gas for the subject breathing. Thus the first limb 8 and the second limb 9 connect lungs of the subject to the ventilator 3 and the gas mixer 5. The ventilator 3 is controlling the breathing circuit pressure through the ventilator connection 4. Also the breathing circuit comprises a housing assembly 10 for removing, such as absorbing, an undesired respiratory gas component of a respiratory gas flow before conveying along the second limb 9 for an inspiration. The housing assembly 10 may comprise only one housing but advantageously as shown in FIG. 2 at least two housings which may be detachable from the breathing circuit and which are a first housing 17 and a second housing 18 in flow communication with each other for removing an undesired expired gas component of the respiratory gas flow before conveying along the second limb for the inspiration.

The housings of the housing assembly may include a substance, which may be solid fluidal material, such as granules for removing an undesired respiratory gas component of a respiratory gas flow. Typical substance used in anesthesia is a carbon dioxide absorbing material, which may be soda-lime, a mixture of calcium hydroxide, sodium hydroxide, potassium hydroxide and water or any other substance that can extract CO2 from gas mixture e.g. molecular sieve or amines. The material may chemically react with carbon dioxide or otherwise remove it from the breathing gas.

Typically the breathing circuit 1 also comprises directional valves 11 and 12 guiding the gas flow in the circuit on direction indicated by arrows 13. For inhalation the ventilator 3 increases the breathing circuit pressure by adding the gas flow from ventilator connection 4. Directional valves 11 and 12 guide the gas flow through the housing assembly 10 to remove in this embodiment carbon dioxide from the breathing gas, to the second limb 9 and further along a subject limb 14 to the subject's lungs 2. For expiration the ventilator 3 releases gases from the breathing circuit through the ventilator connection 4. For this purpose the ventilator 3 may e.g. operate an expiration valve (not shown in Figure). This will allow the gas flow from distended subject's lungs through the subject limb 14 to the first limb 8 and further through the directional valve 12 to the ventilator connection 4. The directional valve 11 prevents the gas flow from the subject's lungs to enter the second limb 9 hereby maintaining the second limb free from CO2. Instead, the exhaled gas is rich of CO2 that needs to be removed before being re-circulated for the inspiration, which is done in the housing assembly 10 including the substance removing carbon dioxide.

Figure 2:
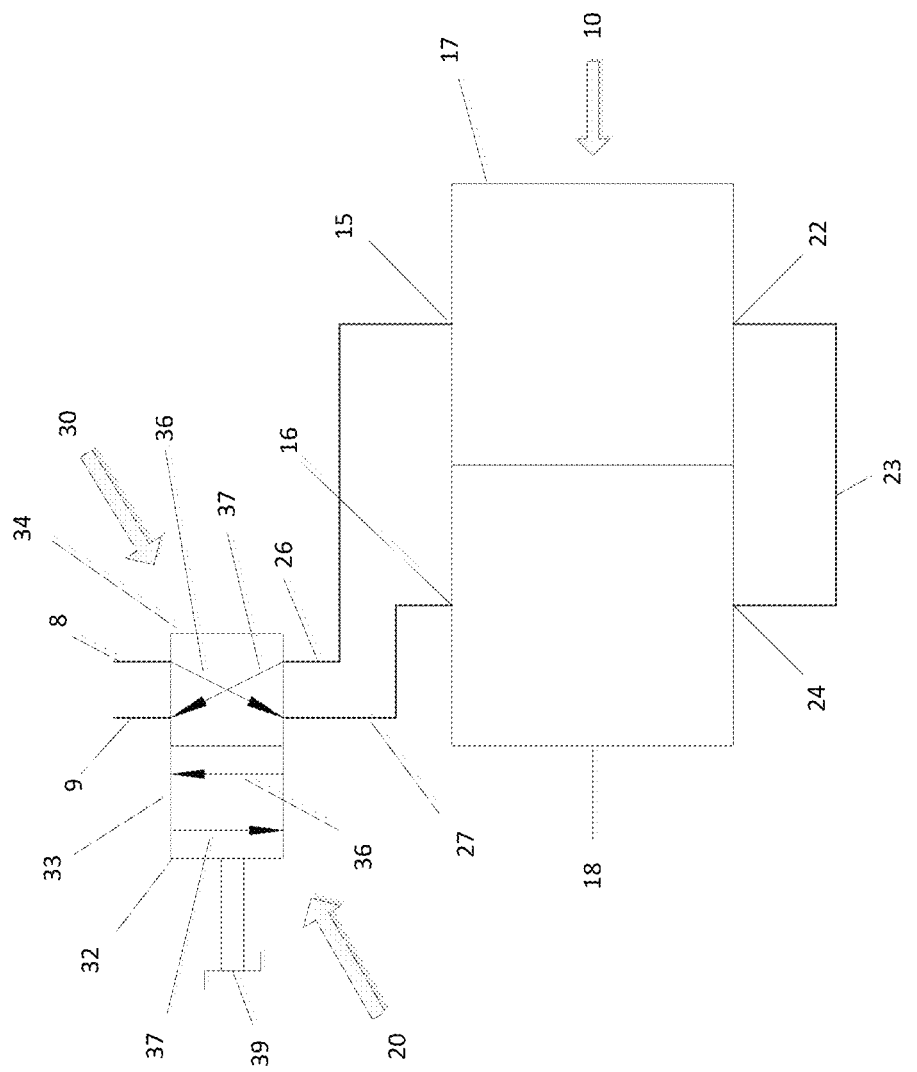
FIG. 2 shows a schematic cross-sectional view of an arrangement for guiding expired respiratory gas flow through a housing assembly for removing an undesired respiratory gas component in accordance with an embodiment.

The breathing circuit 1 further comprises an arrangement 20 shown more detailed in FIG. 2 for guiding expired respiratory gas flow arrived along the first limb 8 through the housing assembly 10. The arrangement 20 may comprise, if desired, a first gas connection 26, such as a channel, and a second gas connection 27, such as a channel, for guiding the respiratory gas flow arrived along the first limb 8 towards the housing assembly 10 and from the housing assembly along the second limb 9 for the subject breathing. Thus one of the first and second gas connections is configured to guide the respiratory gas received along the first limb 8 towards the housing assembly 10 and another one or in this case the remaining one of the first and second gas connections is configured to convey the respiratory gas from the housing assembly 10 along the second limb 9 for the subject breathing.

The arrangement 20 comprises a gas routing device 30, such as a directional valve, for guiding the flow direction, which valve is in flow communication with the first gas connection 26 and the second gas connection 27, if such connections are desirable. The gas routing device 30 as well as the housing assembly 10 through the gas routing device typically is in flow communication with the second limb 9 as shown in FIG. 2 for guiding the respiration gas towards the lungs 2 of the subject, but the gas routing device 30 and the housing assembly 10 is also in flow communication with the first limb 8 receiving the respiratory gas flow. In this specific embodiment the first limb 8 extends to the gas routing device 30 of the arrangement 20 in which case the first limb is directly connected to the gas routing device. Also in this specific embodiment the gas routing device is directly connected to the second limb 9, which means that the gas routing device is between the first limb 8 and the second limb 9. However, it is irrelevant whether the arrangement or the gas routing device locates in the first limb or in the second limb or between these two limbs, but the main thing is that the arrangement 20 or the gas routing device 30 is in flow communication with the breathing circuit or even locates in the breathing circuit where it can receive the expired gas and guide it through the housing assembly 10 and further guide for the inspiration of the subject.

The gas routing device 30 is provided with at least two different route options. According to a first route option the expired gas is guided first through the first gas connection 26 or directly to a first port 15 of the housing assembly 10, through the housing assembly to the second port 16 and then discharged from the second port 16 of the housing assembly through the second gas connection 27 or directly to the gas routing device. According to a second route option the expired gas is guided first through the second gas connection 27 or directly to the second port 16 of the housing assembly 10, through the housing assembly to the first port 15 and discharged from the first port of the housing assembly through the first gas connection 26 or directly to the gas routing device. So the gas flow through the housing assembly can be arranged in opposite directions. The gas flow guided from the housing assembly 10 to the gas routing device 30 is further guided along the second limb 9 for the subject breathing.

In case the housing assembly comprises at least two housings for removing undesired gas component, the gas flow from the first limb 9 is guided by means of the gas routing device 30 either to the first port 15 and through the first housing 17 to the second housing 18 and through the second housing to the second port 16 and discharged to the gas routing device 30 or to the second port 16 and through the second housing 18 to the first housing 17 and through the first housing to the first port 15 and discharged to the gas routing device 30. The decision whether to guide the respiratory gas flow first through the first housing 17 or the second housing 18 can be made for instance by a user, To connect the gas flow between the first housing 17 and the second housing 18, which are side by side, there is a connecting channel 23. The connecting channel 23 may be connected to a first intermediate port 22 of the first housing 17 and a second intermediate port 24 of the second housing 18. The connecting channel 23 is not needed especially in case the first housing and the second housing are one on top of the other. The volume of the connecting channel 23 providing gas flow to both ways is small to minimize the volume inside the anesthesia machine and to minimize cleaning and service and gas dilution. This connecting channel can be made out of plastic which could be either reusable and cleanable or disposable. Furthermore, it could be either connected to the anesthesia machine or completely separate.

The gas routing device 30 in FIG. 2 comprises a body 32 having a first sector 33 and a second sector 34. Both sectors comprise at least two channels, the first routing channel 36 and a second routing channel 37, providing the gas flow connection between the housing assembly and the breathing circuit or its first limb 8 and the second limb 9. Thus the first limb 8 can be connected to one of the first gas connection 26 and the second gas connection 27, and the second limb 9 can be connected to the remaining one of the first gas connection and the second gas connection. The first and second gas connections are not necessarily needed in case the gas routing device can be connected directly to the ports of the housing assembly. In the first sector 33 as shown in FIG. 2 the first routing channel 36 is substantially parallel with the second routing channel 37, in which case the first routing channel 36 is connecting the first limb 8 through the first gas connection 26 or directly to the first port 15 of the housing assembly 10 and the second routing channel 37 is connecting the second limb 9 through the second gas connection 27 or directly to the second port 16 of the housing assembly 10.

In the second sector 34 the first routing channel 36 and the second routing channel 37 are crosswise but passing each other without direct flow connection between the first and second routing channel. Thus the first routing channel 36 connects the first limb 8 through the second gas connection 27 or directly to the second port 16 of the housing assembly 10 and the second routing channel 37 connects the second limb 9 through the first gas connection 26 or directly to the first port 15 of the housing assembly 10.

In FIG. 2 the gas routing device is moving or actually in this specific embodiment sliding or turning from a first position to a second position so that both the first sector 33 and the second sector 34 can be chosen. In the first position, when the first sector 33 has been chosen, the first routing channel 36 of the first sector 33 is connected between the first limb 8 and the housing assembly 10 guiding the breathing gas first through the first gas connection 26 or directly to the first port 15 and through the housing assembly to the second port 16 and through the second gas connection 27 or directly to the second routing channel 37 and to the second limb 9 for guiding the breathing gas substantially free from carbon dioxide to the subject. In case there are at least two housings in the housing assembly the gas flows first through the first housing 17 to the first intermediate port 22 and from this port through the second intermediate port 24 to the second housing 18 and through this second housing to the second port 16.

In the second position, when the second sector 34 has been chosen, the first routing channel 36 of the second sector 33 is connected between the first limb 8 and the housing assembly 10 guiding the breathing gas first through the second gas connection 27 or directly to the second port 16 and through the housing assembly to the first port 15 and through the first gas connection 26 or directly to the second routing channel 37 and to the second limb 9 for conveying the breathing gas substantially free from carbon dioxide to the subject. In case there are at least two housings in the housing assembly the gas flows first through the second housing 18 to the second intermediate port 24 and from this port through the first intermediate port 22 to the first housing 17 and though this first housing to the first port 15.

As explained hereinbefore the gas routing device 30 can be used to choose the direction of the respiration gas through the housing assembly in which case the respiration gas flow direction can be from one of the opposite ports of the housing assembly, which ports are in the embodiment of FIG. 2 the first port 15 and the second port 16. This may be the fact also in case the housing assembly comprises at least two housings directing the gas flow through all these housings one after the other irrespective of whether the housings are side by side or one on the other. The gas routing device of FIG. 2 is manually operated by means of a knob 39 for instance by pushing, pulling and turning it.

In practice for instance the first route option is chosen to guide the expired gas first to the first housing removing the undesired expired gas component of the respiratory gas flow and after that to the second housing removing substantially rest of the undesired expired gas component, if such still exists. The second route option may be chosen to guide the expired gas first to the second housing removing the undesired expired gas component of the respiratory gas flow and after that to the first housing removing substantially rest of the undesired expired gas component, if such still exists, but before operating in accordance with the second option the first housing can be replaced by a new one having more capacity to remove undesired expired gas component than with the used first housing. Typically the housing has been replaced by the new one, when the capacity of the housing is under a predetermined level just because its capacity has been consumed, which can be seen also visually when the color of the substance removing the undesired gas component is changing or the color change is widening to cover the major part of the substance inside the housing.

Figure 3:
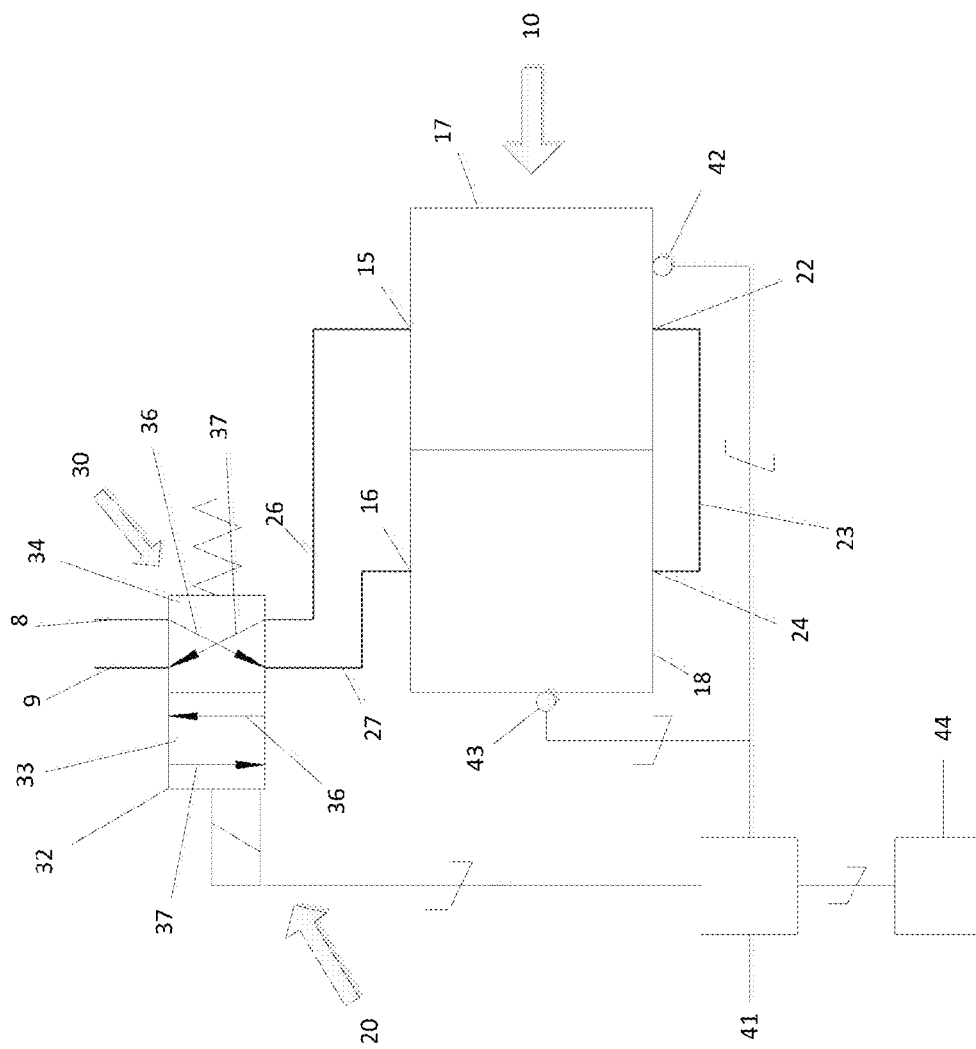
FIG. 3 shows a schematic cross-sectional view of an arrangement for conveying expired respiratory gas flow through a housing assembly for removing an undesired respiratory gas component in accordance with another embodiment.

Another embodiment of an arrangement 20 is shown in more detailed in FIG. 3 for guiding expired respiratory gas flow arrived along the first limb 8 through the housing assembly 10. Same reference numbers are used as in FIG. 2. As a difference compared to the embodiment of FIG. 2, the embodiment of FIG. 3 is electrically operated, but the main principle is same which is to choose the direction of the respiration gas through the housing assembly 10 in which case the respiration gas flow direction can be from one of the opposite ports of the housing assembly, which ports are in the embodiment of FIG. 3 the first port 15 and the second port 16. This may be the fact also in case the housing assembly comprises at least two housings directing the gas flow through all these housings one after the other irrespective of whether the housings are side by side or one on the other.

The functions of the gas routing device 30 in FIG. 3 are similar to the one introduced in FIG. 2, but this gas routing device is electrically operated by means of a control unit 41. The arrangement 20 in FIG. 3 also comprises sensors, such as a first sensor 42 and a second sensor 43 in case of two housings in the housing assembly 10, The more sensors may be needed the more housings are needed. The first housing 17 may be provided with the first sensor 42 and the second housing 18 may be provided with the second sensor 43. The sensors may be signaling a presence of the housings and which housing is a newer one considering the removing capacity of undesired gas component. Also this signal can be used to choose the respiratory gas flow direction through the housing assembly, whether it is guided first through the first housing or the second housing. As explained hereinbefore the gas flow is advantageously guided first through the housing, which is the used one and which typically also includes partly the substance, which is unable to remove or absorb the undesired gas component from the gas flow, which thus includes less the active substance removing undesired gas component from the respiratory gas than the new housing with new active substance. After that housing the gas flow is guided through the new housing including substance having substantially full capacity to remove the undesired gas component from the gas flow.

The signal from the first and second sensors is received by the control unit 41, but shown to the user by means of an indicator 44, such as led change indicator. The signal may indicate to the user the direction of the respiratory gas flow through the housing assembly 10 and which one of the first housing 17 and the second housing 18 should first be changed to a new one, when it is time to do that due to the fact that the capacity to remove undesired gas component like carbon dioxide is insufficient.

Also the arrangement can be provided with a change controller (not shown in Figure) to control that only the housing that is upstream to the flow is available to be replaced and prevent to change the housing which is downstream. In other words the housing which receives first the respiratory gas flow is replaced first, but another housing receiving the gas flow after that is left unchanged. When the new housing has replaced the used one, the flow direction is changed opposite to guide the flow from the housing unchanged to consume its absorbing capacity first and then direct the flow to the new one. This may be advisable to get the full capacity out from an absorber material inside the housing and to avoid replacing such housing which has still a lot of capacity left, but to replace the housing that is exposed to the CO2 gas first. The downstream/upstream position of the housings may be changed by changing the flow direction by means of the gas routing device 30 of the arrangement 20, to avoid by physically changing the housings in respect to each other.

The embodiments described above solve the problem due to inability to fully exploit the capacity to remove the undesired gas component in the housing assembly. Also, when using one of two housings to return the breathing gas to the breathing circuit, cleaning of the bigger amount of parts needed in well-known designs for the gas return to the breathing circuit can be avoided which is an advantage. As well an increased total volume of the housing assembly can be solved by the housing assembly having at least two housings where one of the housings in itself provides a part of the gas return conduit. That is an integrated/inherent gas return conduit to minimize the volume inside the anesthesia machine requiring cleaning and service and diluting gases.

Also, the advantage of the embodiments is the use of both two and multiple housings as well as a single integrated housing design for those users who value more decreased maneuvering needs over increased absorbent use rate.

Typically the housings could be swapped and replaced with a predetermined order. This may be advantageous because in order to get the full capacity out from the housing with the undesired gas component removing substance it needs to be the housing that is exposed to the CO2 gas first. If it was the other way around a premature CO2 breakthrough would happen inhibiting the full usage of the capacity of the housing. With embodiments show in FIGS. 2 and 3 the user does not need to swap around the housings already in use but only replace the one that is used up. The downstream/upstream position of the units is changed by changing the flow direction, not by physically changing the units in respect to each other.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claim.

We claim:

1. An arrangement for guiding expired respiratory gas flow in a breathing circuit through a housing assembly configured to remove an undesired expired gas component of the expired respiratory gas flow before an inspiration of a subject, the housing assembly having a first port and a second port, one of the first port and the second port configured to receive the expired respiratory gas flow and another of the first port and the second port configured to discharge the expired respiratory gas flow, the arrangement comprising:

a gas routing device in flow communication with the breathing circuit and the housing assembly through the first port and the second port, the gas routing device comprising a first routing path and a second routing path, the gas routing device configurable between at least two different route options, wherein the first routing path is connected to the first port of the housing assembly and the second routing path is connected to the second port of the housing assembly in a first route option of the at least two different route options such that the gas routing device is configured to guide the expired respiratory gas flow through the first routing path to the first port of the housing assembly, through the housing assembly to the second port of the housing assembly, and through the second routing path to the breathing circuit for the inspiration, and wherein the second routing path is connected to the first port of the housing assembly and the first routing path is connected to the second port of the housing assembly in a second route option of the at least two different route options such that the gas routing device is configured to guide the expired respiratory gas flow through the first routing path to the second port of the housing assembly, through the housing assembly to the first port of the housing assembly, and through the second routing path to the breathing circuit for the inspiration.

2. The arrangement according to claim 1, further comprising a first gas connection connected to the first port of the housing assembly and a second gas connection connected to the second port of the housing assembly, wherein the first gas connection is connected to the first routing path and the second gas connection is connected to the second routing path in the first route option, and wherein the second gas connection is connected to the first routing path and the first gas connection is connected to the second routing path in the second route option.

3. The arrangement according to claim 1, wherein the gas routing device comprises a body having a first sector for the first route option and a second sector for said second route option, wherein the first sector is selected when the gas routing device is configured for the first route option and the second sector is selected when the gas routing device is configured for the second route option.

4. The arrangement according to claim 3, wherein the first sector comprises a first routing channel and a second routing channel, the first routing channel of the first sector corresponding to the first routing path and the second routing channel of the first sector corresponding to the second routing path when the first sector is selected, and wherein the second sector comprises a first routing channel and a second routing channel, the first routing channel of the second sector corresponding to the first routing path and the second routing channel of the second sector corresponding to the second routing path when the first sector is selected.

5. The arrangement according to claim 1, wherein the gas routing device is electrically operated.

6. The arrangement according to claim 5, further comprising a control unit to electrically operate the gas routing device.

7. The arrangement according to claim 1, wherein the housing assembly comprises at least two housings configured to remove the undesired expired gas component of the expired respiratory gas flow, wherein a first housing of the at least two housings comprises the first port of the housing assembly and a second housing of the at least two housings comprises the second port of the housing assembly.

8. The arrangement according to claim 7, wherein when the gas routing device is configured for the first route option the first housing is configured to remove at least a portion of the undesired expired gas component and the second housing is configured to remove a substantial remaining portion of the undesired expired gas component not removed by the first housing,
    wherein when the gas routing device is configured for the second route option the second housing is configured to remove at least another portion of the undesired expired gas component and the first housing is configured to remove a substantial remaining portion of the undesired expired gas component not removed by the second housing, and
    wherein the first housing is configured to be replaced by a third housing having a greater capacity to remove the undesired expired gas component than a capacity to remove the undesired expired gas component of the first housing.

9. The arrangement according to claim 1, wherein gas routing device comprises a directional valve.

10. A breathing circuit for ventilating lungs of a subject comprising:
    a first limb for guiding expired respiratory gas flow;
    a housing assembly having a first port and a second port, one of the first port and the second port configured to receive the expired respiratory gas flow and another of the first port and the second port configured to discharge the expired respiratory gas flow, the one of the first port and the second port configured to guide the expired respiratory gas flow through the housing assembly to remove an undesired expired gas component of the expired respiratory gas flow;
    a second limb for guiding a gas flow received from the housing assembly for an inspiration; and
    an arrangement for guiding the expired respiratory gas flow through the housing assembly,
    wherein arrangement comprises a gas routing device in flow communication with the first limb, the second limb and the housing assembly through the first port and the second port, the gas routing device comprising a first routing channel and a second routing channel, the gas routing device configurable between at least two different route options,
    wherein the first routing channel is connected to the first limb and the first port of the housing assembly and the second routing channel is connected to the second port in a first route option of the at least two different route options such that the gas routing device is configured to guide the expired respiratory gas flow from the first limb through the first routing channel to the first port of the housing assembly, through the housing assembly to the second port of the housing assembly, and through the second routing channel to the second limb for the inspiration, and
    wherein the second routing channel is connected to the first limb and the first port of the housing assembly and the first routing channel is connected to the second port of the housing assembly in a second route option of the at least two different route options such that the gas routing device is configured to guide the expired respiratory gas flow from the first limb through the second routing channel to the second port of the housing assembly, through the housing assembly to the first port of the housing assembly, and through the first routing channel to the second limb for the inspiration.

11. The breathing circuit according to claim 10, wherein the housing assembly comprises at least two housings configured to remove the undesired expired gas component of the expired respiratory gas flow,
    wherein a first housing of the at least two housings comprises the first port of the housing assembly and a second housing of the at least two housings comprises the second port of the housing assembly, and
    wherein the breathing circuit further comprises a connecting channel providing a flow communication between the first housing and the second housing.

12. The breathing circuit according to claim 11, wherein when the gas routing device is configured for the first route option the first housing is configured to remove at least a portion of the undesired expired gas component and the second housing is configured to remove a substantial remaining portion of the undesired expired gas component not removed by the first housing,
    wherein when the gas routing device is configured for the second route option the second housing is configured to remove at least another portion of the undesired expired gas component and the first housing is configured to remove a substantial remaining portion of the undesired expired gas component not removed by the second housing, and
    wherein the first housing is configured to be replaced by a third housing having a greater capacity to remove the undesired expired gas component than a capacity to remove the undesired expired gas component of the first housing.

13. A method for guiding expired respiratory gas flow in a breathing circuit through a housing assembly for removing an undesired expired gas component of the expired respiratory gas flow before an inspiration of a subject, housing assembly having a first port and a second port, one of the first port and the second port configured to receive the expired respiratory gas flow and another of the first port and the second port configured to discharge the expired respiratory gas flow, the method comprising:
    determining a direction for the expired respiratory gas flow to flow through the housing assembly; and
    configuring a gas routing device between at least two different route options, the gas routing device comprising a first routing channel and a second routing channel,
    wherein the first routing channel is connected to the first port of the housing assembly and the second routing channel is connected to the second port of the housing assembly in a first route option of the at least two different route options such that the gas routing device is configured to guide the expired respiratory gas flow through the first routing channel to the first port of the housing assembly, through the housing assembly to the second port of the housing assembly, and through the second routing channel to the breathing circuit for the inspiration,
    wherein the second routing channel is connected to the first port of the housing assembly and the first routing channel is connected to the second port of the housing assembly in a second route option of the at least two different route options such that the gas routing device is configured to guide the expired respiratory gas flow through the first routing channel to the second port of the housing assembly, through the housing assembly to the first port of the housing assembly, and through the second routing channel to breathing circuit for the inspiration, and
    wherein a direction of the first route option is opposite a direction of the second route option.

14. The method according to claim 13, wherein the housing assembly comprises at least two housings, the method also comprising:

replacing one of the at least two housings another housing having a greater capacity to remove the undesired expired gas component than a capacity to remove the undesired expired gas component of the one of the at least two housings, when the capacity of the at least one of the at least two housings is under a predetermined level.

15. The method according to claim 14, further comprising; determining a second direction for the expired respiratory gas flow to flow through the housing assembly based on which of the at least two housings was replaced; configuring the gas routing device between the at least two different route options based on the determined second direction.

16. The arrangement according to claim 1, wherein the gas routing device is manually operated to select one of the at least two different route options.

17. The arrangement according to claim 16, further comprising a knob for manually operating the gas routing device.

18. The arrangement according to claim 6, wherein the housing assembly comprises a first housing and a second housing, and wherein the arrangement further comprises:

a first sensor coupled to the first housing and the control unit and configured to indicate a capacity of the first housing to remove the undesired expired gas component;

a second sensor coupled to the second housing and the control unit and configured to indicate a capacity of the second housing to remove the undesired expired gas component; and an indicator configured to indicate a direction of the expired respiratory gas flow and configured to indicate when the capacity of the first housing or the capacity of the second housing is insufficient for removing the undesired expired gas component.

* * * * *